United States Patent [19]

Arsenault et al.

[11] Patent Number: 5,646,312

[45] Date of Patent: Jul. 8, 1997

[54] PROCESS OF AQUEOUS EXTRACTION OF MALTOL

[75] Inventors: Raoul Arsenault, Pointe-Claire; Michel Trottier, Sherbrooke; Esteban Chornet, Sherbrooke; Paul Jollez, Sherbrooke, all of Canada

[73] Assignee: Florasynth, Inc., Teterboro, N.J.

[21] Appl. No.: 582,382

[22] Filed: Jan. 3, 1996

[51] Int. Cl.⁶ .................................................. C07D 309/40
[52] U.S. Cl. .................................................. 549/418
[58] Field of Search .................................................. 549/418

[56] References Cited

U.S. PATENT DOCUMENTS

| | | | |
|---|---|---|---|
| 3,501,501 | 3/1970 | Heintz et al. | 549/418 |
| 4,946,695 | 8/1990 | Forster et al. | 426/286 |
| 5,221,756 | 6/1993 | Fleisher et al. | 549/418 |
| 5,301,694 | 4/1994 | Raymond et al. | 131/297 |

OTHER PUBLICATIONS

Fleisher, et al. (May/Jun. 1991) "Water–Soluble Fractions of the Essential Oils", *Perfumer & Flavorist* 16, 37–41.

Goos, et al. "New Products from wood Carbonization", *Industrial and Engineering Chemistry* 38, No. 2, 132–135; Feb. 1946.

LeBlanc, et al. (Apr. 1989) "Maltol and Ethyl Maltol: From the Larch Tree to Successful Food Additive", *Food Technology*, 78–84.

*Primary Examiner*—Johann Richter
*Assistant Examiner*—Laura L. Stockton
*Attorney, Agent, or Firm*—Scully, Scott, Murphy & Presser

[57] ABSTRACT

Disclosed herein is a process where maltol is extracted from a source material containing maltol by employing an aqueous extraction process wherein reverse osmosis is utilized to concentrate an aqueous extract of maltol. The maltol in the concentrated aqueous extract is adsorbed on a bed containing an adsorbent material and then desorbed using a hydrophilic solvent and separated.

21 Claims, 1 Drawing Sheet

PROCESS OF AQUEOUS EXTRACTION OF MALTOL

FIELD OF THE INVENTION

The present invention relates to a process for aqueous extraction of maltol from a source material which contains maltol. Specifically, the process of the instant invention comprises (a) collecting the source material containing maltol; (b) extracting maltol from the source material with water at a temperature less than 70° C., in a series of 5–10 relatively short soak cycles wherein the aqueous extracts from each soak cycle are recovered and combined and each soak cycle begins with fresh water; (c) performing reverse osmosis on the combined aqueous extracts of step (b) to concentrate the maltol; (d) passing the concentrated aqueous extracts of step (c) through a bed containing a suitable adsorbent material, wherein the adsorbent material adsorbs said maltol; (e) desorbing the adsorbed maltol with a hydrophilic solvent; and (f) separating the maltol from the hydrophilic solvent.

BACKGROUND OF THE INVENTION

Maltol (2-methyl-3-hydroxy-4-pyrone) is a heterocyclic aroma chemical used extensively in flavor and fragrance compositions. It is naturally occurring in numerous plant species, especially in coniferous trees such as Larix and Abies spp.

The presence of maltol in various plant sources has been known for many years and considerable efforts have been made to develop a sensible method for its commercial recovery. The existing techniques are rather complex and the use of the resulting maltol is cost-prohibitive.

One means of purifying maltol is by co-distillation with ethylene glycol. The solubility of maltol in ethylene glycol at ambient temperature exceeds 4%. This completely prohibits economical maltol recovery from dilute mixtures, effectively eliminating virtually all natural sources. Moreover, there is a limiting practical consideration being that the crystallization of maltol from ethylene glycol at ambient temperatures is very slow. At low temperatures the viscosity of ethylene glycol also considerably hampers filtration of maltol from ethylene glycol/maltol mixtures.

Ethylene glycol derived maltol is also unsuitable for food application, since the removal of toxic ethylene glycol contaminates from maltol is rather difficult.

Maltol can be obtained in very small amounts from the destructive distillation products of wood, and by a partial synthetic process from kojic acid, which is obtained from fermentation media. However, maltol obtained from such means is quite expensive.

Maltol has also been reported to be in the bark of species of larch trees. Maltol can be present in larch bark in combined form to an extent varying from about 0.1 to about 2 percent by weight depending upon the bark layer and the season harvest. The richest supply of maltol is found in the bark roots of the larch trees although, for practical reasons, not much root bark is harvested. Large quantities of larch trees and bark containing maltol exists and are available primarily in the northwest part of the United States and southwest Canada. The bark is available at sawmills where it is stripped off of larch trees and stored in a pile to be later removed and burned for fuel or to be alternatively used in economical processes for recovering useful components.

It is also known that maltol is present in various parts of coniferous species found in rather low concentrations in the oleoresin extracted from fresh foliage of balsam fir (Abies balsamea L.)

Fleisher & Fleisher, "Water-Soluble Fractions of the Essential Oils", Perfumer and Flavorist, Vol. 16, May/Jun. 1991, pp. 37–41 gives the composition and details of recovery of compounds from fir needles (Abies balsamea L.) and a good biographical literature discussing the recovery of essential oils.

Goos and Reiter, "New Products from Wood Carbonization", Industrial and Engineering Chemistry, Vol. 38, No. 2, February 1946, pp. 132–135 discloses the isolation of maltol in small amounts by fractional distillation of soluble tar fractions.

LeBlanc and Akers, "Maltol and Ethyl Maltol from the Larch Tree to Successful Food Additive", Food Technology, April 1989, pp. 78–84 provides a survey of the historical production, properties and applications of maltol and ethyl maltol.

U.S. Pat. No. 5,221,756 to Fleisher et al. discloses that sufficiently pure maltol can be effectively recovered from oleoresin through the co-distillation with a suitable hydrocarbon and, in particular, alpha-pinene. The process of co-distillation, although, effective, requires a rather complex technological set-up, application of vacuum, high pressure steam and necessary handling of flammable liquids. Moreover, during co-distillation, maltol crystallizes directly from the gaseous phase in a microcrystalline form. Thus, maltol obtained from co-distillation processes retains substantial quantities (30 to 40%) of the hydrocarbon which complicates further purification.

On the other hand, fir balsam resin is a valuable product for the perfume industry for its fine delicate organoleptic qualities. During co-distillation this material can suffer from long exposure to high temperatures which alters the organoleptic profile of the resin and consequently reduces its value.

Despite the current state of the art there remains a continued need to provide a process for aqueous extraction of maltol from source materials containing maltol that provide commercial quantities of maltol which are in a substantially pure state. The present invention provides such a process for the recovery and purification of maltol without excessively large expenditures in equipment and raw materials.

SUMMARY OF THE INVENTION

The present invention is directed to a process for aqueous extraction of maltol from a source material containing maltol which comprises the steps of (a) collecting the source material containing maltol; (b) extracting maltol from the source material with water at a temperature less than 70° C., in a series of 5–10 relatively short soak cycles wherein the aqueous extracts from each soak cycle are recovered and combined and each soak cycle begins with fresh water; (c) performing reverse osmosis on the combined aqueous extracts of step (b) to concentrate the maltol; (d) passing the concentrated aqueous extracts of step (c) through a bed containing a suitable adsorbent material which is capable of adsorbing said maltol; (e) desorbing the adsorbed maltol with a hydrophilic solvent; and (f) separating the maltol from the hydrophilic solvent. The foregoing process provides maltol that has a purity from about 89% to about 99.99%.

The adsorbent material employed in the present invention can be any solid adsorbent material which has a high affinity for maltol. That is, the adsorbent material has a high ability to adsorb maltol. Exemplary adsorbent materials that can be used in the instant invention include cellulose, polymer resins, starch, sugars, magnesium silicate, silicic acid, silica gel, florisil, aluminum oxide, activated charcoal and the like. In a preferred embodiment of the instant invention the support material is activated carbon.

The hydrophilic solvents that can be used in the instant invention to desorb the maltol off the adsorbent material include alcohols, esters, ketones, aldehydes, carboxylic acids, ethers and alkyl halides. The preferred hydrophilic solvent is an alcohol, with methanol being most preferred.

BRIEF DESCRIPTION OF THE DRAWING

The FIGURE is a flow chart of a preferred embodiment of the present invention.

DETAILED DESCRIPTION OF THE INVENTION

Figure 1:
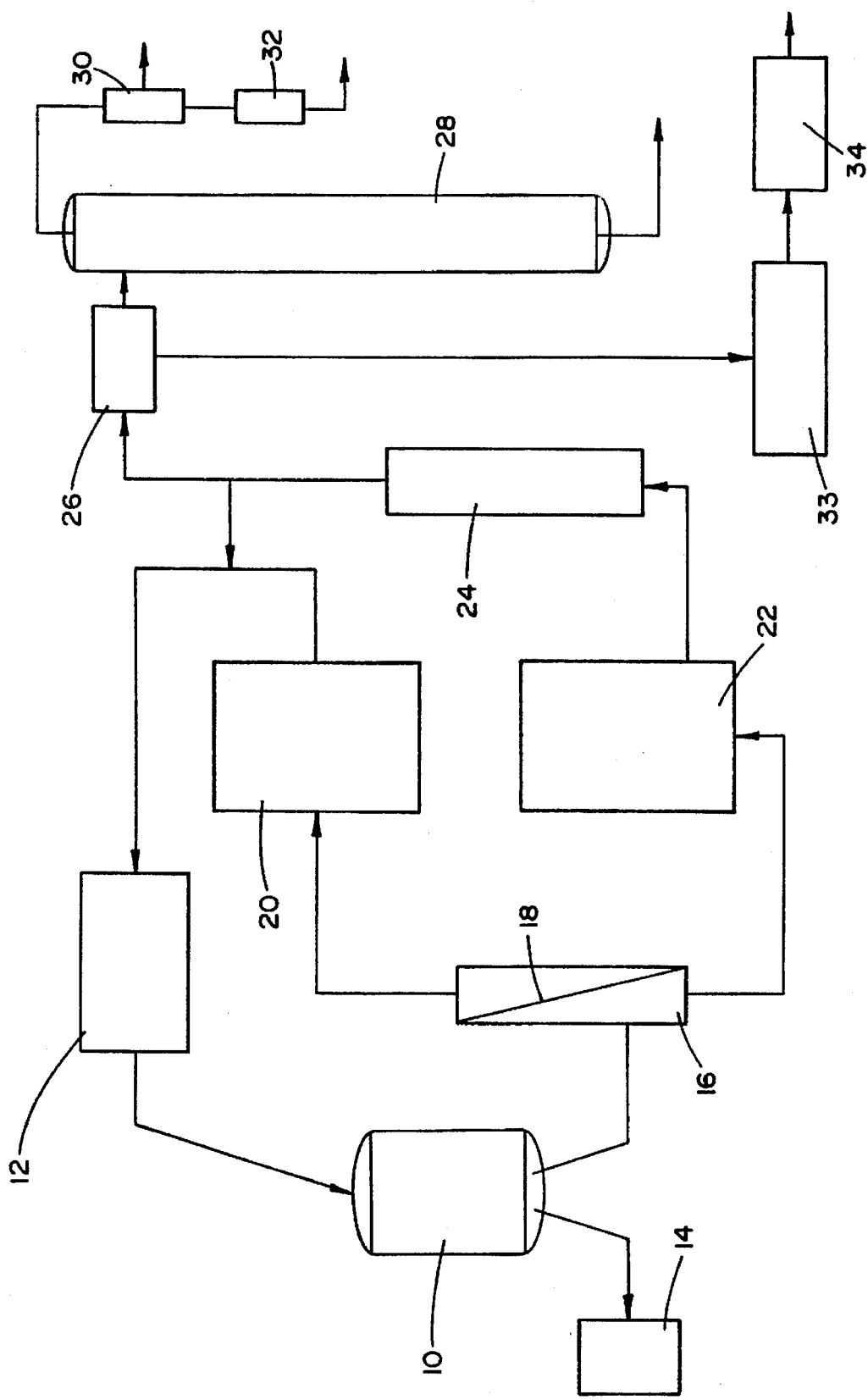

The present invention is useful for extraction and recovery of maltol from source material containing maltol. The source material employed in the instant invention includes fresh as well as dehydrated plant materials which contain maltol. By fresh it is meant that the source material is hydrous; i.e. it contains water. Suitable source material employed in the present invention includes needles, leaves, bark, branches and other plant materials. A particularly preferred source material is fir foliage, including needles and small branches. Another preferred source material is larch foliage or bark. It is a particularly preferred embodiment of the present invention that the source material be fresh branches of larch or fir foliage. When hydrous source material is employed in the present invention the moisture content can range from 1 wt. % up to 50% or higher.

In accordance with the present invention, the source material containing maltol is first collected using conventional methods that are well known in the art and then the collected material is subjected to extraction using water as the extractant. Other extractants beside water are also contemplated by the present invention.

More specifically, the extraction process employed in the instant invention utilizes water as a low temperature solvent to extract maltol from the source material. The extraction process comprises loading the source material into an extraction tank, spraying water on the top of the loaded source material until the extraction tank is filled, allowing the water to infuse through the loaded source material, draining off the infused water and transpiring the wet source material.

The extraction steps mentioned hereinabove are conducted at a temperature of from about 30° C. to about 70° C. More preferably, the temperature range employed during the extraction process is from about 40° C. to about 65° C.

Typically in the present invention, the extraction process requires about 5 to about 10, more preferably about 6 to about 9, short soak cycles to preform about 80 to about 90% maltol extraction in each cycle. By short soak cycle it is meant that each cycle takes about 1 to about 15 minutes to perform. After each soak cycle, the aqueous extracts containing maltol are recovered using conventional methods well known to those skilled in the art and combined. It is emphasized that each new extraction cycle begins with fresh water.

The extraction process of the instant invention utilizes from about 7 to about 15 cubic meters of water per ton of source material loaded into the extraction tank. More preferably, the instant invention employs from about 12 to about 14 cubic meters of water per ton of loaded source material.

The aqueous extract that results from the above extraction process is a dilute extract which contains, in addition to maltol, various sugars, such as xylose and glucose, as well as lignin-related colloids and other naturally occurring color agents. The resultant aqueous extract must be processed rapidly, otherwise fermentation of the aqueous extract can take place. Maltol is generally present in the dilute aqueous extract in a range from about 200 to about 600 ppm. More preferably, the dilute aqueous extract contains from about 350 to about 450 ppm maltol.

Next, the aqueous extract from the aforementioned extraction process is subjected to reverse osmosis which operates preferably in a batch mode. Reverse osmosis serves to concentrate the dilute aqueous extract that is produced in the extraction process. Typically, the dilute aqueous extract is concentrated by at least about 2:1, more preferably at least about 5:1 to about 10:1 to 25:1 or higher. More preferably, the concentration achieved is about 20:1.

In accordance with the present invention, the aqueous extract is transferred to a tank that contains a reverse osmosis membrane which is permeable to the extractant, i.e., water, but not permeable to maltol and the other naturally occurring compounds present in the dilute aqueous extract.

In order to effect reverse osmosis in the present invention, the pressure gradient of the dilute aqueous extract entering the tank must be larger and opposite to the osmotic pressure gradient of maltol. Typically, in the present invention this requires that a pressure of about 300 to about 600 psig be exerted on the aqueous extract. More preferably, reverse osmosis is achieved by exerting a pressure of about 400 to about 600 psig on the aqueous extract that enters the reverse osmosis tank.

The permeate that passes through the membrane consists predominately of water which can be recycled and used again in the extraction process. On the other hand, the concentrated liquor which does not pass through the membrane is then transferred to the adsorption stage of the present invention.

As stated above, reverse osmosis serves to concentrate the maltol, as well as the other naturally occurring products, that are present in the source material. The resultant maltol concentration may vary over a wide range depending upon the yield in the aqueous extraction step, and on the loss of maltol which occurs through the unwanted permeation of maltol through the reverse osmosis membrane. Typically, the maltol in the concentrated liquor, after reverse osmosis, ranges from about 2000 to about 10,000, more preferably from about 4000 to about 8000, ppm.

The concentrated liquor from the reverse osmosis stage is then fed to a column that contains a bed of a solid adsorbent material which is suitable for adsorbing maltol but not the other concentrated products in the concentrated liquor. The column is packed using conventional techniques that are well known in the art. The volume of the adsorbent bed may vary, depending on the flow rate. Suitable adsorbent materials that can be employed in the present invention include cellulose, polymer resins, starch, sugars, magnesium silicate, silicic acid, silica gel, florisil, aluminum oxide and activated carbon. Preferably, the adsorbent is activated carbon.

When activated carbon is employed as the adsorbent, the activated carbon is preferably granular in shape and it has a size ranging from about 7 to about 10 μm. Moreover, when the adsorbent material is activated carbon, the adsorption ratio employed in the present invention is about 6.5 to about 8.0% w/w of maltol by weight of dry activated carbon.

The temperature of the adsorption step of the instant invention is preferably from about 50° C. to about 70° C. Moreover, the flow rate of the concentrated liquor that is added to the column must be calculated to allow a residence time of from about 1 to about 2 hours. Typically, the corresponding flow rate can accordingly be calculated.

Prior to adsorption of the maltol onto the adsorbent material, the adsorbent should be treated to remove any contaminants that may adversely affect the maltol that is adsorbed on the material. For example, when activated carbon is employed as the adsorbent material, the adsorbent is treated by washing with fresh water. This eliminates the presence of oxygen in the adsorbent material and thus avoids the oxidation of maltol that may be catalyzed by activated carbon. Other means for treating the adsorbent material that can be employed in the present invention include acid washing, dehydration, and the like.

For the reasons stated hereinabove, adsorbed maltol needs to be quickly desorbed off the activated carbon. That is, to avoid contamination of the desorption solvent with the concentrated liquor, the remaining liquor that is not adsorbed onto the adsorbent must be removed prior to desorption. This is carried out in the present invention by washing the adsorbent material containing adsorbed maltol with cold water followed by purging the system with an inert gas, such as nitrogen or argon.

In the next step of the present invention, maltol is desorbed from the adsorbent by contacting the adsorbent material with a hydrophilic solvent. Specifically, the hydrophilic solvent employed is one that has a higher affinity for maltol than does the adsorbent material. Suitable hydrophilic solvents that can be employed in the present invention include straight chain or branched alcohols containing from about 1 to about 8, preferably about 1 to about 4, carbon atoms; straight chain or branched esters containing from about 2 to about 8, preferably about 2 to about 6, carbon atoms; straight chain or branched ketones containing from about 3 to about 8, preferably from about 3 to about 6, carbon atoms; straight chain or branched aldehydes containing from about 1 to about 8, preferably about 1 to about 4 carbon atoms; straight chain or branched carboxylic acids, containing from about 1 to about 8, preferably about 1 to about 4, carbon atoms; straight chain or branched ethers containing from about 2 to about 8, preferably about 2 to about 6, carbon atoms; and alkyl halides, containing from about 1 to about 8, preferably about 1 to about 6, carbon atoms.

Exemplary alcohols that can be used in the present invention include methanol, ethanol, propanol, t-butanol, pentanol and the like. Of these alcohols, methanol is highly preferred.

Suitable esters that can be employed in the instant invention are methyl acetate, propyl acetate and the like. Of the esters listed herein, methyl acetate is particularly preferred.

Exemplary ketones that can be employed as the hydrophilic solvent are acetone, 2-butanone, 2-pentanone, 3-pentanone and the like. Acetone is a particularly preferred ketone that may be used in the present invention.

Suitable aldehydes that can be utilized in the instant invention are formaldehyde, acetaldehyde, propanol, butanol, pentanol, benzaldehyde and the like. Of the aldehydes, acetaldehyde is particularly preferred.

Exemplary carboxylic acids that may be employed as the hydrophilic solvent include formic acid, acetic acid, propionic acid, butyric acid, valeric acid, 2,2-dimethylpropanoic acid, pivalic acid, oxalic acid, malonic acid, succinic acid and the like.

Exemplary alkyl halides include methyl chloride, methyl bromide, methyl iodide, ethyl chloride, ethyl bromide, ethyl iodide, propyl chloride, propyl bromide, propyl iodide and the like.

In accordance with a preferred embodiment of the instant invention, the hydrophilic solvent is an alcohol, with methanol being the most preferred alcohol.

In the present invention, the desorption process is conducted at a temperature of from about 30° C. to about 60° C., more preferably from about 40° C. to about 50° C. The ratio of hydrophilic solvent to be used depends on the solvent, but typically in the present invention about 3 to about 7 liters of hydrophilic solvent is employed for each kilogram of adsorbent material present in the column. More preferably, the ratio of hydrophilic solvent is from about 5 to about 6 liters per kilogram of adsorbent material. To ensure complete desorption of maltol off the adsorbent material, the residence time for desorption is in the range from about 1 to about 4 hours.

The solvent phase containing maltol is then transferred to an evaporator in order to concentrate the maltol and evaporate off the solvent. In accordance with the present invention, the evaporation temperature is maintained below about 90° C. in order to ensure that none of the maltol is vaporized and carried off in the vapor phase. The vapor phase that flows out of the evaporator has a water content of about 5 to about 15% w/w and it has to be rectified in a distillation column in order to separate the water and to recirculate the solvent back to the desorption stage.

The concentrated maltol-containing solution from the evaporator is then cooled down to a temperature of about −10° C. to about 10° C. in order to crystallize the maltol which is then recovered by techniques that are well known in the art. For example, maltol can be recovered by either centrifugation, decantation or filtration. The maltol crystals that are produced in the present invention have a red color and contain a maltol content of about 89% or higher.

The recovered liquid not containing crystals of maltol can be sent to a water treatment plant or evaporated in a small batch vacuum evaporator in order to recover the solvent content and the residual maltol that is not recovered above. After complete evaporation, the solvent phase is sent to a distillation column and the maltol is recovered from the solids by sublimation with a gas stream having a temperature of greater than about 100° C.

A purification step may then be optionally performed in order to bring the purity of the crystals higher than about 99.9%. In accordance with this embodiment of the instant invention, the crystals obtained in the crystallization process are dissolved in a hot, clean solvent stream having a temperature of greater than about 100° C. and then recrystallized using the steps indicated above for crystallization. The remaining solvent from this purification step is then sent back to the first evaporation stage.

Referring to the accompanying figure, in FIG. 1, tank 10 is an extraction tank into which the collected source material containing maltol is loaded. Water from exchanger 12 is pumped into the top of tank 10 until the extraction tank is filled. The material is soaked in the water for 1–15 minutes, following which the maltol-enriched water is drained to a holding tank (not shown). After repeating the above extracting process approximately 6 times, the soaked source material is transferred to unit 14 wherein water is removed from the source material and is transferred to a water treatment unit not shown.

The resultant combined dilute aqueous extracts from extraction tank 10 is transferred from the tank to osmosis unit 16 which contains an osmotic membrane 18. Reverse osmosis is then conducted and the water that passes through membrane 18 is transferred to reservoir 20. The water from reservoir 20 is recycled to exchanger 12 to be used again in extraction tank 10.

The concentrated material that does not pass through membrane 18 is drained off to reservoir 22. The material is then transferred and pumped into the adsorption unit 24. The adsorption unit 24 contains a bed of an adsorbent material not shown in FIG. 1.

The concentrated material containing maltol is then passed through the adsorbent material at a rate sufficient for maltol to be adsorbed to the adsorbent material. The water that passes through the adsorption unit is transferred to a water treatment unit, not shown, for purification.

To desorb the maltol off the adsorbent material, a hydrophilic solvent is charged into the adsorption unit 24. Maltol from the eluent is then recovered as follows.

The eluent containing maltol is transferred to evaporator 26 which, in accordance with the present invention, is maintained at a temperature below about 90° C. The resultant vapor phase which forms is then transferred to distillation column 28 wherein the solvent and water are removed from the top of the distillation column 28 to condenser 30 and exchanger 32. The pure solvent that exits exchanger 32 is reused again in the desorption process.

During the evaporation process, concentrated maltol-containing solution which exits the bottom of evaporator 26 is then subjected to crystallization and recovered as stated hereinabove.

Specifically, the concentrated maltol that exits the bottom of evaporator 26 is transferred to crystallizer 33 wherein crystals of maltol are formed by cooling the concentrated maltol solution down to a temperature of from about −10° C. to about 10° C. The solution containing the maltol crystals is then transferred to centrifuge 34 whereat the maltol crystals are recovered therefrom.

The above preferred embodiments are given to illustrate the scope and spirit of the invention. These embodiments will make apparent to those skilled in the art other embodiments, which are also within the contemplation of the instant invention. Therefore, the present invention should be limited only by the appended claims.

What is claimed is:

1. A process for aqueous extraction of maltol from a source material containing maltol comprising the steps of:
   (a) collecting the source material containing maltol;
   (b) extracting maltol from the source material with water at a temperature less than 70° C., in a series of about 5 to about 10 relatively short soak cycles wherein the aqueous extracts from each soak cycle are recovered and combined and each soak cycle begins with fresh water;
   (c) performing reverse osmosis on the combined aqueous extracts of step (b) to concentrate the maltol;
   (d) passing the concentrated aqueous extracts of step (c) through a column containing a bed of adsorbent material, wherein the adsorbent material adsorbs said maltol;
   (e) desorbing the adsorbed maltol with a hydrophilic solvent; and
   (f) separating the maltol from the hydrophilic solvent.

2. The process of claim 1 wherein the source material is a hydrous plant material.

3. The process of claim 2 wherein the source material comprises fir foliage or larch foliage.

4. The process of claim 1 wherein the extraction step (b) is conducted at a temperature of from 30° C. to about 70° C.

5. The process of claim 1 wherein from about 6 to about 9 soak cycles are employed in the extraction step.

6. The process of claim 1 wherein the aqueous extract of step (a) is a dilute solution containing from about 200 to about 600 ppm maltol.

7. The process of claim 6 wherein the aqueous extract of step (a) contains from about 350 to about 450 ppm maltol.

8. The process of claim 1 wherein reverse osmosis is conducted to provide a concentration ratio of at least 2:1.

9. The process of claim 8 wherein the concentration ratio is at least 20:1.

10. The process of claim 1 wherein the adsorbent material is a solid adsorbent material selected from the group consisting of cellulose, polymer resins, starch, sugar, magnesium silicate, silicic acid, silica gel, florisil, aluminum oxide and activated carbon.

11. The process of claim 10 wherein the adsorbent material is activated carbon.

12. The process of claim 11 wherein the activated carbon is granular in shape and has a size ranging from about 7 to about 10 μm.

13. The process of claim 1 wherein the adsorption step is conducted at a temperature of from 50° C. to about 70° C. and at a residence time of from about 1 to about 2 hours.

14. The process of claim 1 wherein the hydrophilic solvent comprises a straight chain or branched alcohol containing from about 1 to 8 carbon atoms; a straight chain or branched ketone containing from about 3 to about 8 carbon atoms; a straight chain or branched aldehyde containing from about 1 to about 8 carbon atoms; a straight chain or branched carboxylic acid containing from about 1 to about 8 carbon atoms; a straight chain or branched ether containing from about 2 to about 8 carbon atoms; a straight chain or branched ester containing from about 2 to about 8 carbon atoms; or an alkyl halide containing from about 1 to about 8 carbon atoms.

15. The process of claim 14 wherein the hydrophilic solvent is an alcohol or an ester.

16. The process of claim 15 wherein the alcohol is methanol.

17. The process of claim 1 wherein the desorption step is conducted at a temperature of from about 30° C. to about 60° C. for a period of time of from about 1 to about 4 hours.

18. The process of claim 1 wherein said separation step includes the steps of evaporation, distillation and crystallization.

19. The process of claim 18 wherein said evaporation step is conducted at a temperature below 90° C.

20. The process of claim 1 further comprising (g) purifying the recovered maltol.

21. The process of claim 20 wherein the purification step comprises recrystallizing the recovered maltol at a temperature of from −10° C. to 10° C.

* * * * *